United States Patent [19]

Searle

[11] Patent Number: 5,386,727
[45] Date of Patent: Feb. 7, 1995

[54] DYNAMIC RAIL LONGITUDINAL STRESS MEASURING SYSTEM

[75] Inventor: Donald S. Searle, St. Joseph, Mo.

[73] Assignee: Herzog Contracting Corporation, St. Joseph, Mo.

[21] Appl. No.: 25,937

[22] Filed: Mar. 3, 1993

Related U.S. Application Data

[63] Continuation-in-part of Ser. No. 892,183, Jun. 2, 1992, Pat. No. 5,341,683.

[51] Int. Cl.$^6$ ............................................. G01N 29/26
[52] U.S. Cl. ........................................ 73/602; 73/624; 73/636; 73/639
[58] Field of Search .............. 73/597, 599, 602, 624, 73/625, 627, 628, 636, 639, 635, 641, 642

[56] References Cited

U.S. PATENT DOCUMENTS

| | | | |
|---|---|---|---|
| 3,937,068 | 2/1976 | Joy | 73/636 |
| 3,962,908 | 6/1976 | Joy | 73/636 |
| 4,004,455 | 1/1977 | McKee et al. | 73/615 |
| 4,044,594 | 8/1977 | Owens et al. | 73/621 |
| 4,165,648 | 8/1979 | Pagano | 73/625 |
| 4,167,879 | 9/1979 | Pedersen | 73/610 |
| 4,174,636 | 11/1979 | Pagano | 73/636 |
| 4,235,112 | 11/1980 | Kaiser | 73/634 |
| 4,429,570 | 2/1980 | Norris | 73/636 |
| 4,457,178 | 7/1984 | Turbe et al. | 73/636 |
| 4,468,966 | 9/1984 | Bradshaw | 73/636 |
| 4,662,224 | 5/1987 | Turbe | 73/636 |
| 4,689,995 | 9/1987 | Turbe | 73/636 |
| 4,700,574 | 10/1987 | Turbe | 73/636 |
| 4,932,618 | 6/1990 | Davenport et al. | 246/122 R |
| 5,020,371 | 6/1991 | Panetti | 73/636 |

Primary Examiner—Hezron E. Williams
Assistant Examiner—Rose M. Finley
Attorney, Agent, or Firm—Litman, McMahon & Brown

[57] ABSTRACT

A system and method for dynamically and non-destructively measuring the longitudinal stresses in a rail of a continuous rail track includes an ultrasonic transmitter which transmits a signature coded pulse pattern through a rail which pulse pattern is altered by the rail section dependent upon the longitudinal stress within the rail. The altered pulse pattern is then received and a data processor, in conjunction with a rail height detector, a rail temperature detector, and a rail splice detector, dynamically determines the longitudinal stresses in the rail as a function of the received pulse characteristics and calculates the stress free temperature (SFT) of the rail. A rail marker marks portions of the rail having unacceptable SFT values. Stress and related rail data are recorded on a data log. A position sensor provides milepost positions to three decimal places.

43 Claims, 7 Drawing Sheets

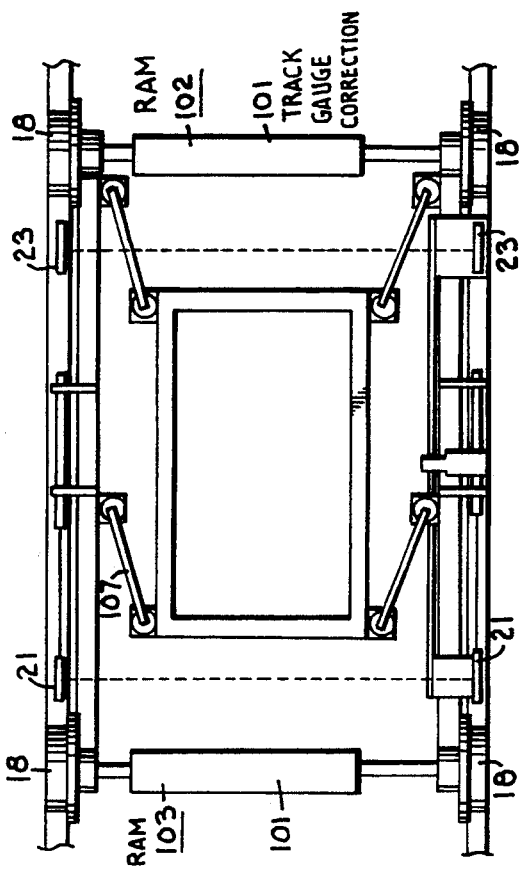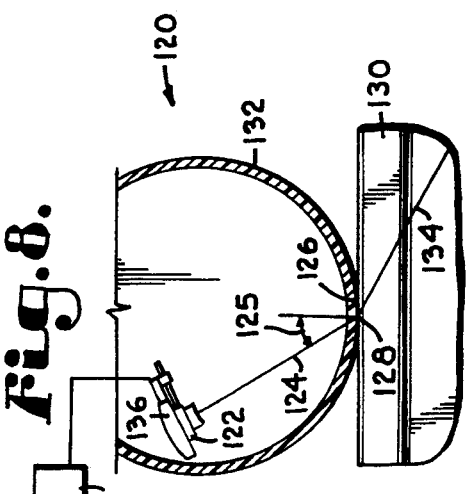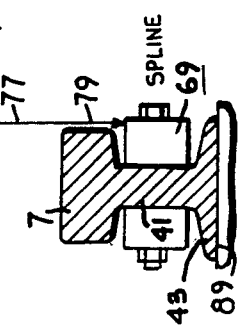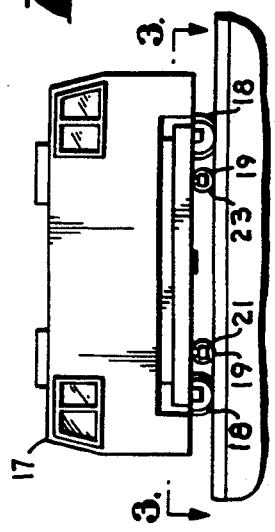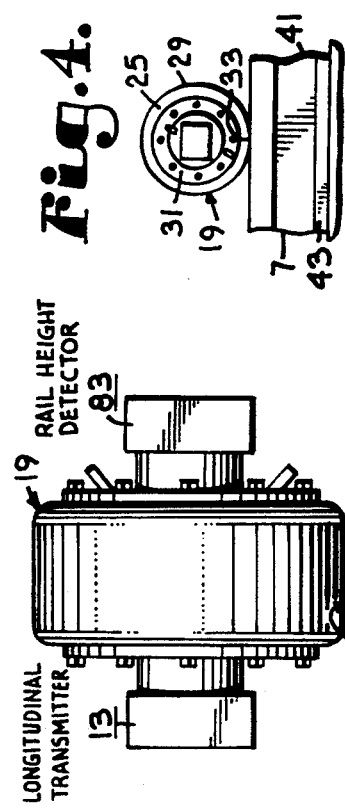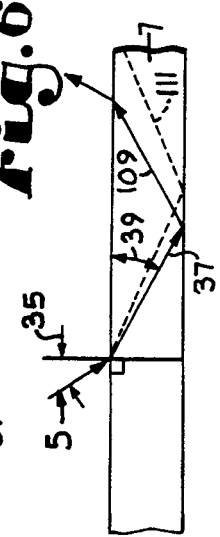

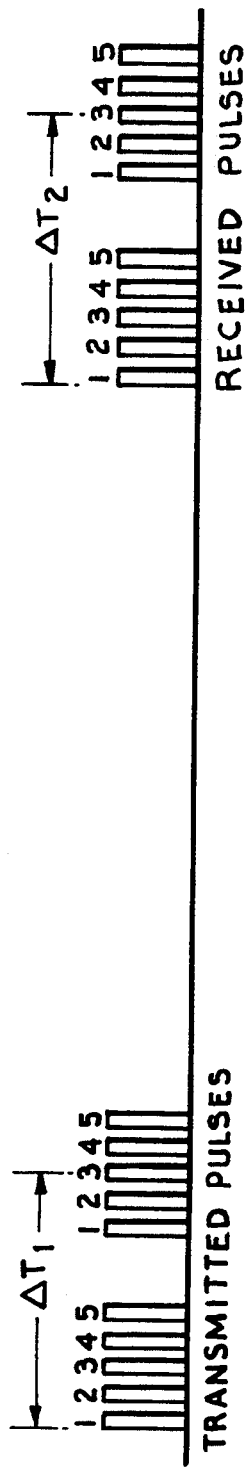
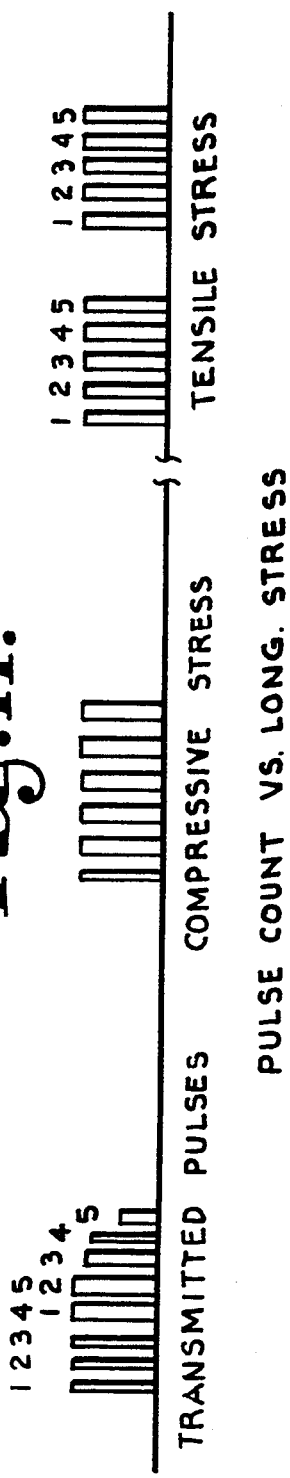

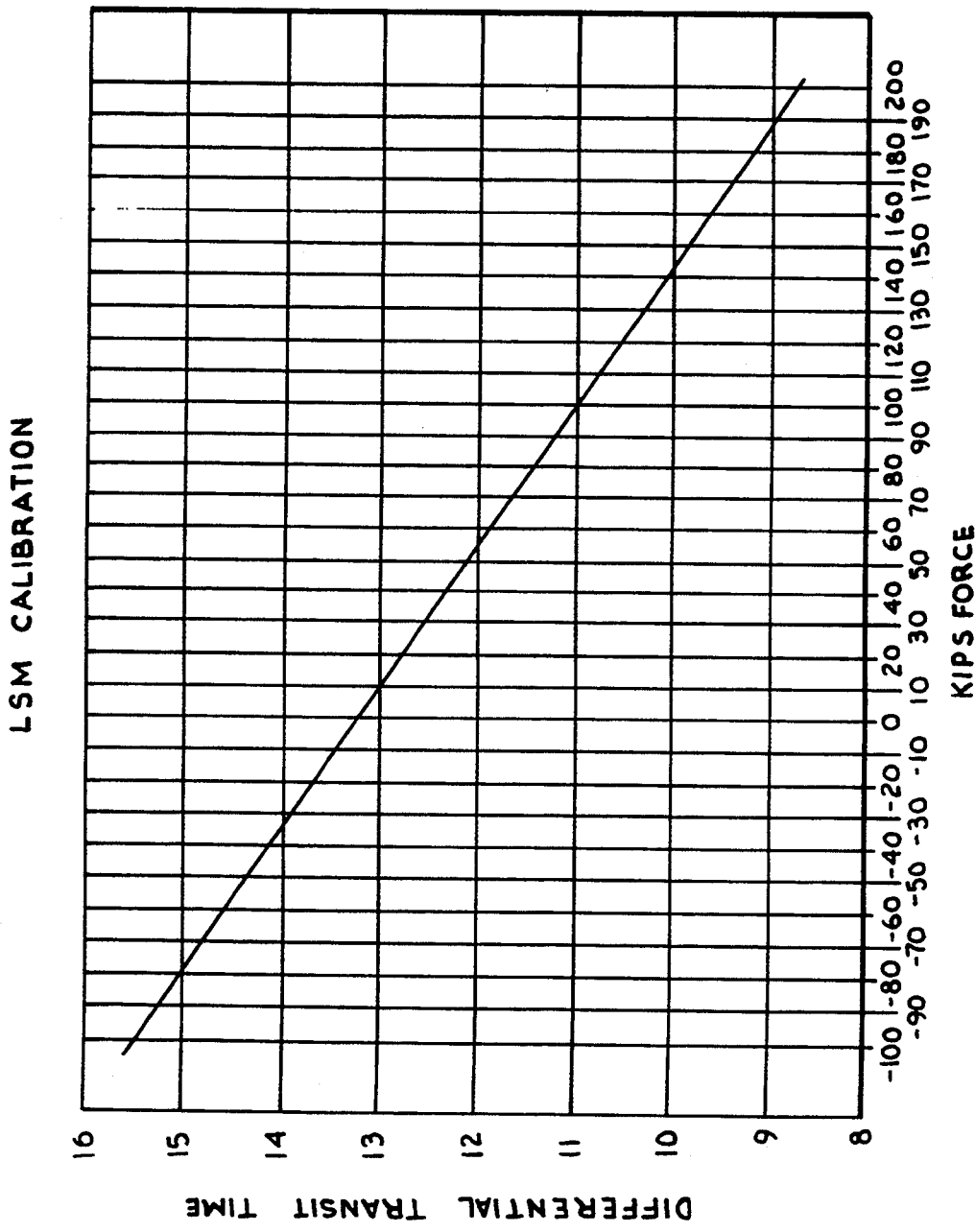
Fig. 10. LSM CALIBRATION

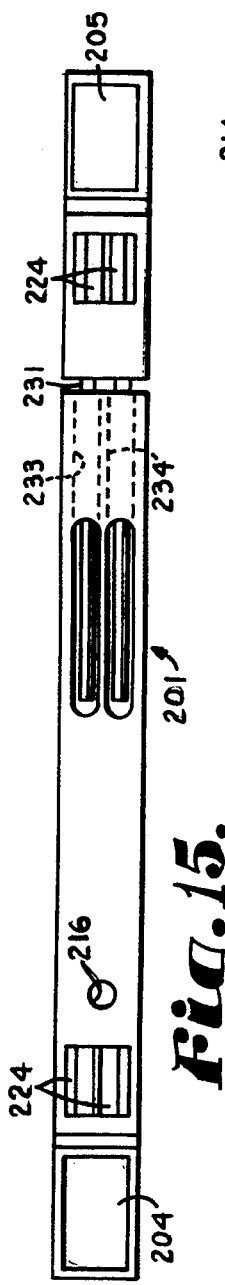
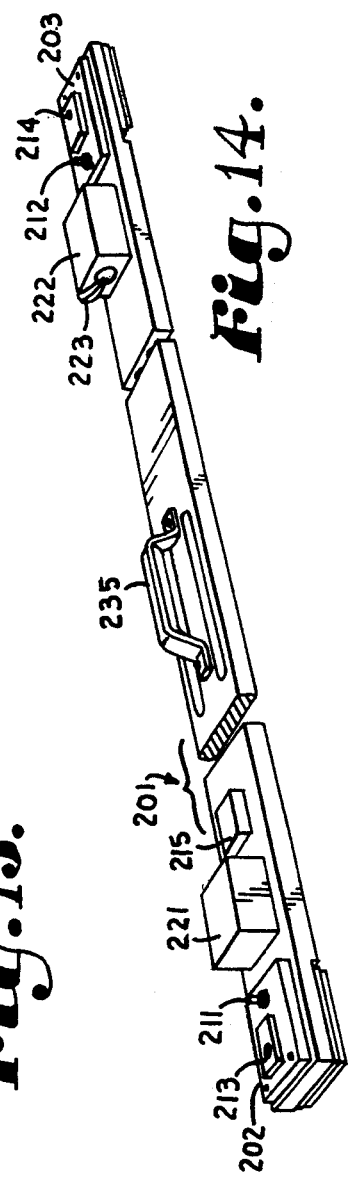
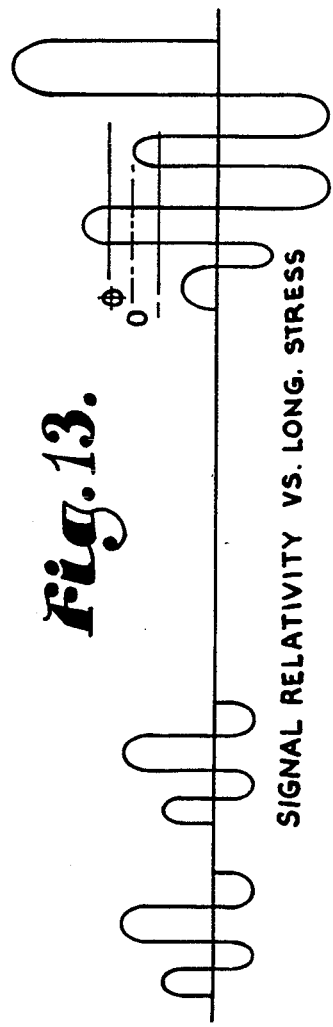
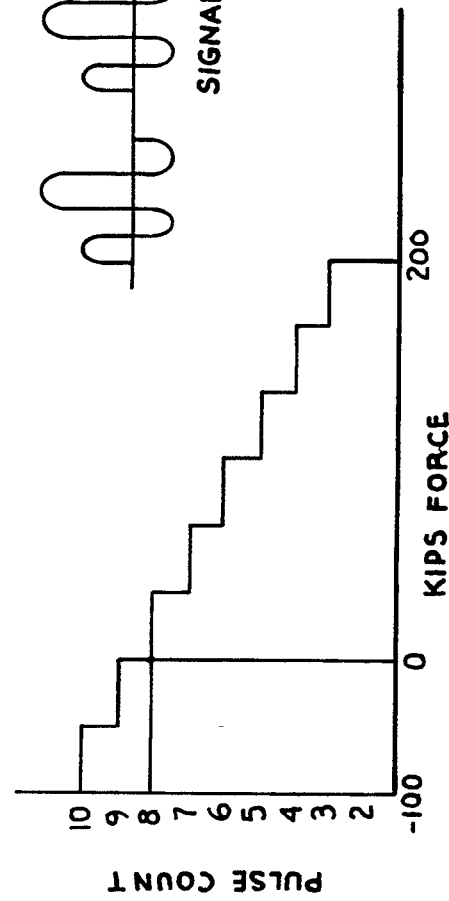
Fig. 15.
Fig. 14.
Fig. 13.
Fig. 12.

DYNAMIC RAIL LONGITUDINAL STRESS MEASURING SYSTEM

CROSS-REFERENCE TO RELATED APPLICATION

This is a continuation-in-part of copending U.S. patent application, Ser. No. 07/892,183, filed Jun. 2, 1992, now U.S. Pat. No. 5,341,683, entitled DYNAMIC RAIL LONGITUDINAL STRESS MEASURING SYSTEM, said application being incorporated herein by reference.

BACKGROUND OF THE INVENTION

1. Field of the Invention

The present invention relates to an apparatus and method for measuring the stress in an elongate steel member and, specifically, without limitation, for dynamically measuring the longitudinal stress in each rail of a railroad track having continuous rails.

2. Description of the Related Art

In the past, railroad tracks have largely been constructed by anchoring discrete rail sections having finite length to an underlying road bed in an end-to-end relationship. A distinct advantage provided by such an arrangement is that differences in thermal coefficient of expansion between the metal rail sections and the road bed is absorbed by mechanical joints or gaps, which are purposefully provided between adjacently spaced sections as the rail sections are installed. Unfortunately, those gaps cause substantial maintenance problems, which generally require lifting and aligning selected ones of the rail sections, reconstruction of the sub-grade or road bed, and the like. Besides added maintenance problems, the mechanical joints also cause ride, noise and comfort problems.

During the last three decades, an effort has been underway to eliminate the mechanical joints in railroad tracks. That effort has largely involved constructing tracks having continuous rails by welding or otherwise joining together the ends of the adjacently spaced rail sections, forming a structure sometimes referred to as continuous rail track, or "CR" track. The technology associated with the construction of a CR track is well known in the prior art.

The elimination of mechanical joints from rail tracks by joining together the rail section ends, however, creates new problems arising from seasonal variations in the ambient temperature. In tropical climates, the ranges between the temperature extremes are generally moderate, which does not pose a substantial problem for rail systems. In temperate climates, however, such as those in the United States, Asia, Australia and Europe, the ranges of temperature extremes are sufficient to cause catastrophic, temperature induced failures in rail systems, including both rail pull-apart and rail-buckle failures, as hereinafter described.

For example, an unanchored 100-mile length of continuous rail in certain areas of a temperate climate could experience a change in length of over 700 feet from one seasonal temperature extreme to the other. By anchoring the rail to railroad ties, changes in the overall length of the rail can be largely prevented but, instead, resultant localized longitudinal stresses are created internally in the rail.

As the rails of a CR track are initially installed and anchored to a road bed, each of the rails has zero longitudinal stresses. The temperature at which the CR track is installed is sometimes referred to as the stress-free temperature, or "SFT".

As the ambient temperature falls below the SFT, tensile longitudinal stresses are created internally in each rail of the CR track due to the greater thermal coefficient of expansion of the metal rails relative to that of the underlying road bed. If the difference between the reduced ambient temperature and the SFT is extreme, the tensile stresses in the rails can potentially attain sufficient magnitude to actually cause one or both of the rails to pull apart.

Preferably, a CR track is installed at a temperature such that the magnitude of the maximum, cold-temperature induced, tensile stresses are substantially less than those required to produce a rail pull-apart. If one or both of the rails of a CR track should pull apart in extremely cold conditions, risk exposure for derailment is generally minimal as pull-apart failure usually occurs beneath a moving train and the resulting separation between the two ends at the pull apart may not be sufficient to cause derailment. Failure to anchor the track at an appropriate SFT, however, may result in much larger separations—gaps of up to 6 inches have been recorded—which do pose a serious threat of derailment.

Fortunately, pull-apart failure can easily be detected by establishing an electrical track circuit using the rails as part of the conduction path, which becomes "open" if one of the rails of the CR track pulls apart.

Similarly, as the ambient temperature climbs above the SFT, compressive stresses are created internally in each of the rails of the CR track. If the difference between the elevated ambient temperature and the SFT is extreme, the compressive stresses in the rails can potentially attain sufficient magnitude to actually cause one or both of the rails to buckle. Theoretical calculations indicate that a stress of approximately 200 Kips (kilopounds) is sufficient to cause rail buckle during extreme Summer temperatures. (Strictly speaking, stress is a measure of force per unit area; however, since the cross-sectional area of a given rail is substantially constant, the expression herein of longitudinal rail stress in force units should be interpreted to mean force per cross-sectional area of the rail.)

Such buckling, which is random, unpredictable and a major source of derailments, generally occurs as a result of the CR track being anchored at a temperature whereby excessive compressive stresses are generated in the rails during peak Summer temperatures. The ability of a train to negotiate a lateral rail displacement, which is typical of rail-buckle, is minimal. As a result, rail-buckle poses a substantially greater risk of derailment than does a rail pull-apart since the former cannot be detected by a conventional track circuit.

To reduce the risk of failures occurring during both upper and lower temperature extremes, the rails of a CR track are generally anchored to the underlying road bed at a preferred SFT, or "PSFT" which is generally situated approximately mid-way between the upper and lower extreme temperatures normally realized for each locality containing the rails. The PSFT is generally defined as the CR installation temperature at which the CR track, hopefully, will not fail due to rail pull-aparts during extremely cold ambient temperatures, nor fail due to rail-buckle during extremely hot ambient temperatures.

The PSFT for any particular locality should take into account several variables, including temperature extremes, rail size and cross-section, track structure design, curves and tangent lengths, rail anchor design, tie type and weight, number of anchors per tie, track geometry and profile, ballast modulus, etc. If anchoring of the continuous rails occurs at temperatures substantially removed from the PSFT for a particular locality, the risk that the track may fail either from rail pull-apart or from rail-buckle is substantially enhanced.

For example, in one locality in Wyoming, the rails of a CR track are generally constructed of 136 lb./yd. rail stock and are generally anchored at a PSFT of approximately 95° F. (In a 136-lb./yd. rail, industry standards indicate that the longitudinal stresses change by approximately 1.8 Kips/° F.) In Wyoming, rail temperature extremes ranging from −50° F. to 160° F. have been recorded. Therefore, rail-buckle can occur if a CR track is anchored at ambient temperatures substantially below the PSFT of 95° F.

In one instance during extreme Winter conditions, a rail of a CR track pulled apart with the width of the resulting gap between the two rail segments indicating that a stress of approximately 300 tons/inch$^2$ had caused the failure. If the rail had been properly installed at the PSFT of 95° F., then an ambient temperature of −50° F., or temperature differential of 145° F. from the PSFT, would have been insufficient to develop the indicated catastrophic tensile stress.

Even if a CR track is anchored at the PSFT, the desired stress characteristics arising therefrom are compromised each time a railroad maintenance crew routinely repairs fatigue defects in the track, which repairs occur with a frequency of approximately 200,000 annually within North America alone. The inability to reestablish the PSFT characteristics at each site after such repair results in previously unascertainable, cumulative deviations of the actual longitudinal rail stresses of the repaired rail from those which preferably would exist relevant to the PSFT. Destruction of the preferred internal stressing characteristics is accentuated for repairs which are performed during extreme temperature conditions.

For example, the installation of a rail insert, sometimes referred to as a "plug", in extremely cold ambient temperatures far below the PSFT can result in relieving the existing tensile stresses which would otherwise have countered a certain portion of the compressive stresses anticipated to arise during the hot Summer season.

Similarly, the opposite effect is realized if a stress-free plug is inserted in extremely hot ambient temperature, far above the PSFT, which then substantially aggravates the excessive, relatively localized tensile stresses occurring during the cold Winter season.

The seasonality of the longitudinal stresses, complicated by the continuity interruptions, resulting from maintenance and repair of rail fatigue and other defects, is believed to cause the existing longitudinal rail stresses to be largely unknown, thereby making predictability of rail-buckle failures virtually impossible.

Even if the rails of a CR track are installed at or near the PSFT, each of the rails and the road bed are dynamic systems. Thus, absolute longitudinal stresses in the rails need to be periodically monitored and controlled.

The economic consequences of derailments is substantial. In 1989, the FRA reported that within the United States alone, rail induced derailments caused damages of approximately $56,000,000. Although not all of those derailments arose from a single type of cause, rail-buckles were responsible for a significant portion of those damages, not to mention the concurrent loss of life.

Although various methods and apparatus have been developed in an attempt to prevent rail-buckle in a CR track, none of them are capable of dynamically, accurately, and non-destructively measuring the absolute longitudinal stress in the rails of a CR track. For example, traditional methods for determining longitudinal stresses in a rail of a CR track include severing the rail, observing the resultant gap or closure between the severed ends, and analyzing the width of the gap or closure as a function of the ambient temperature. Obviously, this method is a destructive and undesirable procedure.

Fortunately, the propagation velocity of ultrasound through a continuous rail varies as a function of the magnitude of the internal stresses of the rail. Unfortunately, however, other methods and apparatus utilizing ultrasonic techniques for detecting various types of flaws and defects in rails have suffered from interference arising from flange noise. Flange noise is generated as the flanges of the wheels of a deployable vehicle containing the apparatus roll along the rails such that multi-point contact is made between the rails and the wheels at different rolling diameters, thereby causing a situation sometimes referred to as "slip".

The sound spectrum generated by slip generally spans a particular ultrasonic frequency, such as 2.25 MHz., which could be usefully employed to measure longitudinal stresses. Without filtering or otherwise minimizing the effects of the flange noise, the randomness and magnitude of this interference is sufficient to mask the useful data which could otherwise be obtained by ultrasonic techniques.

It has long been recognized that the time of flight of an ultrasonic signal through a rail varies as a function of the longitudinal stress in the rail. However, with chemistry and metallurgical effects also changing the flight time, it has been virtually impossible to isolate the flight time change which is directly attributable to longitudinal stress. Accordingly, other, more reliably measurable relationships between ultrasonic transmission characteristics and longitudinal stress must be utilized.

What is needed is an apparatus and a method which can be used to minimize or eliminate the effects of sonic interference from flange noise and which, therefore, can be used to dynamically and non-destructively measure the absolute longitudinal stresses in the rails of a CR track. Such an apparatus and method must use ultrasound characteristics other than a straight time of flight measurement, since no technique has been created to measure a reliable, isolatable longitudinal stress effect using this variable.

SUMMARY OF THE INVENTION

An improved rail stress measuring system is provided for dynamically and non-destructively measuring the longitudinal stresses in a rail of a continuous rail track. The system includes an apparatus having an ultrasonic transmitter which transmits coded, focused shear wave pulses which are refracted longitudinally through a rail. The transmitted pulses are subsequently received by a plurality of sensors which are arranged in an array aligned with the axis of the rail. A focusser collimates the transmitted pulses and focusses them on the array. The outputs of each of the sensors is filtered by one of a plurality of filters which are tuned to the coded pulses, thereby eliminating interference from other extraneous sources of ultrasonic waves, such as those arising from rail squeal or flange noise.

In one stress measurement technique, a displacer adjusts the separation between the transmitter and the sensors to maximize the signal intensity received by a centrally located one of the sensors relative to the signal intensities received by other ones of the sensors situated on either side of the centrally located sensor. The displacer also adjusts the equilibrium configuration, as the angle of refraction changes due to changes in the velocity of propagation of the pulses through the rail which varies as a function of the longitudinal stresses in the rail. A displacement encoder communicates the changes in the separation between the transmitter and the sensors to a data processor.

A modified embodiment of a rail stress measuring system is adapted to alter the angle of incidence of the transmitted pulses to adjust for changes in velocity of propagation through the rail caused by changes in longitudinal stress.

The system includes a method for dynamically and non-destructively measuring the longitudinal stresses in a rail of a continuous rail track as a function of changes in the angle of refraction of an ultrasonic shear wave transmitted through the rail. Alternatively, the modified system also includes a method for dynamically and non-destructively measuring the longitudinal stresses in a rail of a continuous rail track as a function of changes in the angle of incidence of an ultrasonic shear wave transmitted through the rail.

A disadvantage inherent in both of the above techniques is that a precise mechanical adjustment mechanism, adjusting the longitudinal spacing between the transmitter and the sensors, in the case of the angle of refraction method, or angularly in the case of the angle of incidence adjustment method, must be incorporated in the apparatus. This requirement for a dynamic mechanical adjustment capability greatly increases its cost, complexity and maintenance requirements. Furthermore, the speed at which the system can operate is limited by the response time of the mechanical adjustment mechanism.

Another disadvantage of the above methods is that both methods are amplitude dependent. This raises a number of problems. With the flange and other ultrasonic noise present in railroad rails, interference with the transmitted signal can affect the amplitude. Also, due to rail surface conditions, changes in metallurgy, etc. it is often difficult to substantially direct an ultrasonic signal into a railroad rail. For these reasons, plus the phenomena of differential pulse transit times, to be explained below, the amplitude of that portion of the signal which actually reaches the receiver can be substantially different from the one which was transmitted.

Accordingly, to limit or eliminate the complexity and add to the speed of operation, other relationships between the transmitted and received signals and the rail longitudinal stress have been developed. These relationships are preferably not amplitude dependent due to the problems inherent in reliably sensing signal amplitude.

In one such relationship, it has been found that, when two successive trains of signature pulses are transmitted, the differential transit time between equivalent pulses in each train varies as a function of the rail longitudinal stress. This is due to the effect of applied longitudinal stress shortening or lengthening the differential time between equivalent pulses and interacting in the nodes and anti-nodes between the pulses. Thus, longitudinal rail stress can be measured simply by sensing the reception times of equivalent pulses in each train and calculating the differential between these equivalent pulse reception times and the equivalent, known differential in the transmitted pulse trains. A linear relationship has been found to exist between applied stress and the differential pulse transit time.

In another such relationship, it has been found that, when two trains of signature pulses are transmitted, the interaction between transmitted signature pulse trains varies with applied longitudinal stress. The net effect of this phenomena is that, as compressive stress is applied, the interaction between two signature wave trains causes the received wave to be distorted to reflect a combination of the two wave trains. This effect is related to the differential transit time described above. Thus, with an increase in compressive stress, the differential transit time between the equivalent pulses decreases, eventually causing one end of the second signature pulse train to merge with the opposite end of the first pulse train. This results in a vectorial addition of the merged ultrasound pulses and a progressive decrease in the number of received pulses. If the pulses are initially transmitted as partially overlapping, the method can also be used to detect tensile stress as well, since the number of received pulses will actually increase. Thus, longitudinal compressive and tensile stress can be measured by simply counting the number of received pulses and contrasting this with the number of transmitted pulses. With the extreme simplicity inherent in such a technique, a relatively simple, hand held longitudinal rail stress measurement apparatus can also utilize this relationship.

Finally, a further relationship between pulse train characteristics and longitudinal stress is the pulse signal amplitude relativity versus longitudinal stress. Again related to the pulse differential transit time, this effect also occurs during compressive stresses when two successive signature wave trains are merged. The vectorial addition of the merged ultrasound wave trains results in a varying relative amplitude level between successive waves in the received, composite wave train. While exact measurements of longitudinal stresses have not been developed using this technique, it has been found that, at least a determination of compressive vs. tensile stress and a gross approximation of the amount of either can be detected by simply detecting and comparing the amplitude of two successive received waves. Although this method is amplitude dependent, it depends upon a relative amplitude between two successive waves, and not an absolute value. Therefore, attenuation of the signature wave does not influence the applicability of the method.

With each of the above techniques, other variables must be provided as inputs as well. Therefore, to detect these variables, a rail height detector comprising an ultrasonic transmitter/receiver arrangement is adapted to dynamically determine the height of the rail by measuring the transit time of an ultrasonic signal transmitted perpendicularly through the rail. A rail temperature detector is adapted to dynamically and remotely determine the temperature of the rail by infra-red techniques. Finally, a rail splice detector comprising a transmitter/receiver arrangement is adapted to dynamically determine the boundaries between individual rail sections of the continuous rail by detecting the splines generally used to connect the rail sections in an end-to-end configuration. The rail splice detector alerts the data processor of the boundary to prevent the rail stress measurement apparatus from unsuccessfully seeking to measure ultrasound transit characteristics across the detected rail gap where, of course, no transmission will occur.

A site identifier identifies the site at which each of the pulses was transmitted through the rail, which information is communicated to the data processor.

The data processor, which determines the longitudinal stresses in the rail as a function of any one or more of the above-defined relationships, calculates the current longitudinal rail stress at the current ambient rail temperature and then derives the stress free temperature (SFT) of the rail at that point. The SFT can then be compared with the preferred SFT for the locality of each of the test sites. For those portions of the rail having current longitudinal stresses and/or SFT's beyond acceptable limits, the data processor activates a rail marker, which appropriately marks the rail with coded data providing the corrective measures needed to adjust the SFT to within acceptable limits.

Stress and related data is recorded on a data log for selected ones of the pulse sites. A video camera provides observed rail separation data to the data processor for comparison with desired rail separation.

PRINCIPAL OBJECTS AND ADVANTAGES OF THE INVENTION

Therefore, the principal objects and advantages of the present invention include: providing an apparatus and method for measuring the absolute longitudinal stresses in a rail of a continuous rail track; providing such an apparatus and method for dynamically measuring the absolute longitudinal stresses in a rail of a continuous rail track; providing such an apparatus and method for ultrasonically measuring the longitudinal stresses in a rail of a continuous rail track; providing such an apparatus and method which determines changes in the longitudinal stress in a rail of a continuous rail track from changes in the angle of refraction of an ultrasonic pulse transmitted into the rail; providing such an apparatus and method which determines changes in the longitudinal stress in a rail of a continuous rail track from changes in the angle of incidence required to maintain the triangulation of an ultrasonic pulse transmitted through the rail; providing such an apparatus and method which determines changes in the differential transit time between equivalent pulses in a transmitted and received pulse train; providing such an apparatus and method which determines changes in the number of received pulses relative to the number of transmitted pulses in a series of trains of such pulses; providing such an apparatus and method which determines changes in the relative amplitude between successive received waves in a series of transmitted trains of such waves; providing such an apparatus and method which minimizes or eliminates the effects of flange noise interference; providing such an apparatus and method which non-destructively measures the absolute longitudinal rail stress in a rail of a continuous rail track; providing such an apparatus and method which prescribes moderate-ambient-temperature corrective repairs for minimizing or eliminating rail failures at extreme ambient temperature conditions by conducting ultrasonic measurements at ambient temperatures; providing such an apparatus and method for measuring both compressive and tensile longitudinal stresses in rails of a continuous rail track; providing such an apparatus and method which can be easily adapted to field measurement; providing such an apparatus and method which can be easily deployed on a deployable vehicle; providing such an apparatus and method which can also be adapted for use with a hand-held ultrasonic transmitter/receiver; providing such an apparatus and method which can be utilized to measure longitudinal rail stresses in different types of track, such as track with either wood or concrete ties, tangent track, curved track, and the like; providing such an apparatus and method for enabling a user to predict the anticipated extreme longitudinal stresses in a rail at the temperature extremes expected for a particular locality based on measurements taken in that locality at a moderate ambient temperature; providing such an apparatus and method which can be used in conjunction with routine rail maintenance repairs without creating unwanted stress characteristics in the rail; and generally providing such an apparatus and method with is reliable and efficient, provides long-life, requires minimal maintenance, and generally provides the benefits for its intended purposes.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 2 is a side elevational view at a reduced scale of a rail deployable vehicle on which the dynamic rail stress measuring system of the present invention can be carried during operation.

FIG. 3 is an enlarged fragmentary plan sectional view taken on line 3—3 of FIG. 2 and illustrates further details of the system vehicle of FIG. 2, including a track gauge correction mechanism of the system.

FIG. 4 is a fragmentary side elevational view of a test wheel deployable with the rail stress measuring system.

FIG. 5 is a greatly enlarged transverse sectional view of the test wheel illustrated in FIG. 4.

FIG. 6 is a diagrammatic view illustrating the propagation path of ultrasonic pulses employed in the rail stress measuring system of the present invention.

FIG. 7 is greatly enlarged transverse sectional view illustrating a boundary detector transceiver of the present invention.

FIG. 8 is a greatly enlarged fragmentary side elevational view illustrating a second embodiment of the rail stress measuring system in which a displacement between the ultrasonic transmitter and receiver is constant and an angular orientation of the transmitter is varied.

FIG. 9 is a time line vs. pulse amplitude graph representing a differential transit method of measuring longitudinal stress.

FIG. 10 is a Kips force vs. differential transit time graph representing the differential transit time method of measuring longitudinal compressive stress.

FIG. 11 is a time line vs. pulse amplitude graph representing a pulse count method of measuring longitudinal compressive stress.

FIG. 12 is a time line vs. pulse amplitude graph representing the pulse count method of measuring longitudinal compressive stress.

FIG. 13 is a Kips force vs. wave amplitude graph representing the signal relativity method of measuring longitudinal compressive stress.

FIG. 14 is a perspective view of a hand-held ultrasonic transmitter/receiver according to a third embodiment of the present invention.

FIG. 15 is an enlarged, bottom plan view of the hand-held ultrasonic transmitter/receiver of FIG. 14.

DETAILED DESCRIPTION OF THE INVENTION

Figure 1:
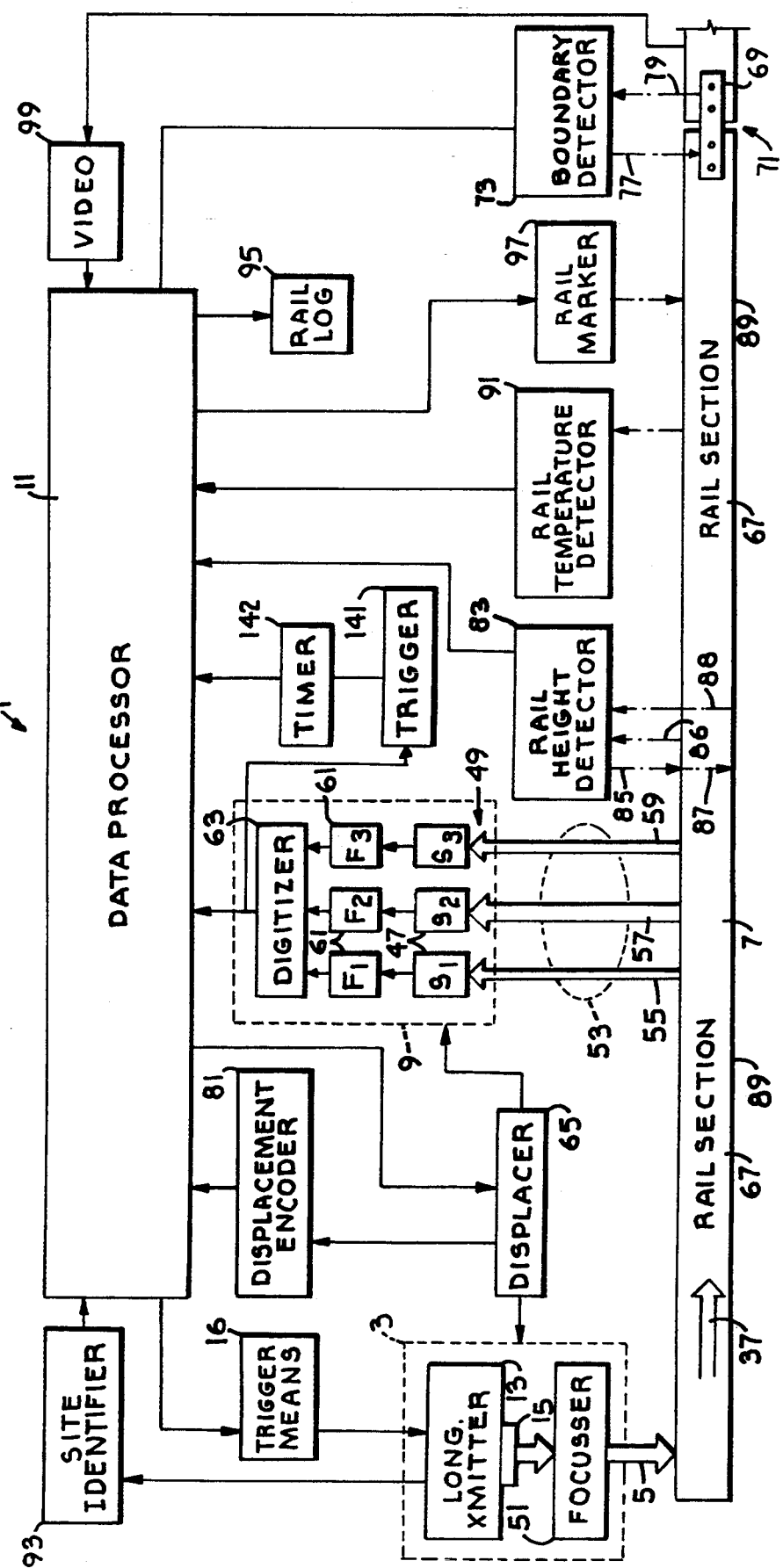
FIG. 1 is a block diagram illustrating the principal functional components of a dynamic vehicle-mounted rail longitudinal stress measuring system embodying the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

1. Stress Induced Displacement (SID) Longitudinal Stress Measurement System

The reference numeral 1 generally refers to a first embodiment of a dynamic rail longitudinal stress measuring system in accordance with the present invention, as shown in FIGS. 1 through 10. It is to be understood that many of the applications of the system 1 involves the measurement of longitudinal stress in each rail of a two-rail track. In that case, such applications generally would utilize two of the systems 1, one for each of the rails of the track. To simplify the following discussion, however, the system 1 as applicable for a single rail will be described.

The system 1 generally includes transmitting means 3 for transmitting an ultrasonic pulse 5 generally longitudinally through a rail 7, receiving means 9 for receiving the transmitted ultrasonic pulse 5, and analyzing means 11 for analyzing the longitudinal stress in the rail 7 as a function of the velocity of propagation of the pulse 5 through the rail 7, as hereinafter described.

The transmitting means 3 generally includes a first or longitudinal transmitter 13, such as Model No. AEG100 as provided by Posstech, Inc., Guernsey, Wyo., or the like, which transmits ultrasonic pulses longitudinally through the rail 7. A coder 15, such as Model No. POST1 as provided by Posstech, Inc., or the like, is adapted to impress a coded configuration or signature upon the pulse 5 transmitted by the longitudinal transmitter 13. Triggering means 16, such as a shaft encoder, Part No. 924-01002-5721 as provided by BEI Motion Systems, or the like, is adapted to trigger the transmitter 13 to periodically transmit the coded pulse 5 at selected intervals along the rail 7, such as every 10 mm. or other suitable time or distance interval.

The system 1 can be mounted on a deployable vehicle 17 (FIG. 2) having two mated pairs of flanged wheels 18 and two mated pairs of test wheels 19, each pair having first and second roller units 21 and 23. Each of the test wheels 19 has a peripheral portion 25 (FIG. 4) constructed of neoprene plastic or other suitable membrane-like, flexible material, which forms a cavity 27 within the respective test wheel 19. Each of the cavities 27 contains a fluid 29.

A transducer, (not shown but similar to the transducer 122 in FIG. 8), in communication with the transmitter 13, which transmits the pulse 5, is mounted such that the pulse 5 is directed into the rail 7 at a first interface 33 between the rail 7 and the peripheral portion 25 of the first roller unit 21 of the vehicle 17 such that the pulse 5 propagates through the rail 7. The transmitter 13 is oriented such that the pulse 5 is directed at a selected angle of incidence 35 (FIG. 6), which generates a refracted pulse 37 having an angle of refraction 39, whereby the refracted pulse 37 is a shear wave. In one application of the present invention, the angle of refraction 39 used to provide a shear wave in the rail 7 was approximately 70°. The transmitter 13 is directed such that the refracted pulse 37 propagates through a web 41 of the rail 7 towards a base 43 of the rail 7 whereat the pulse 37 is internally reflected in the rail 7.

Preferably, the fluid 25 contained in the cavities 27 generally comprises an anti-freeze-type material, such as a suitable mixture of water and ethylene glycol, calcium chloride, or the like. The composition of the fluid 25 is selected to provide a relatively constant velocity of propagation of the pulse 5 therethrough even though the temperature of the fluid 25 may vary.

For example, the fluid 25 may have three parts of water to two parts of ethylene glycol and be maintained at approximately 85° F. Under those conditions, the velocity of propagation of ultrasonic waves therethrough is 1,608 meters/second, which is relatively constant over a temperature variation of approximately ±50° F. For more exact measurements, a thermostat and heater (not shown) can be inserted within the wheel 19 to maintain the fluid 25 at a constant value, and thus maintain the propagation speed at a constant figure.

The receiving means 9 (FIG. 1) generally includes a plurality of receiver transducers or sensors 47 spaced in a linear array 49, which is aligned with the axis of the rail 7. FIG. 1 illustrates one of the arrays 49 having three of the sensors 47—designated "$S_1$", "$S_2$", and "$S_3$". It is to be understood that the array 49 may have any number of the sensors 47.

In one example, the array 49 had eight of the sensors 47 and three of those sensors 47, equidistantly spaced, were selected for use of the system 1. It is foreseen that for applications requiring fewer than all of the sensors 47 in the array 49, the selected sensors 47 may be adjacently spaced or include other non-used sensors 47 spaced therebetween. The sensors 47 are generally spaced such that the reduction of signal amplitude varies by approximately 0.5 db between adjacently spaced ones of the sensors 47.

The system 1 generally includes beam focusing means or focusser 51, such as a lens constructed of lucite or other suitable material or lens configuration, adapted to appropriately focus and collimate the pulse 5 such that the refracted pulse 37 forms an emitted pulse 53 which is refracted and emitted from the rail 7. The pulse 5 is focused such that divergence of the pulse 5, prior to reception of the emitted pulse 53 by the receiving means 9, is minimized. For example, the pulse 5 is focused whereby the image thereof is slightly converging at the receiving means 9, with the image having a diameter of approximately 10 mm.

The emitted pulse 53 is shown as having three components in FIG. 1, designated by the numerals 55, 57, and 59, respectively. It is to be understood, however, that the intensity or signal amplitude of the pulse 5 is greatest along the axis of the pulse 5, which is intended for the sensor $S_2$ and which is diagrammatically represented by the pulse component 57 in FIG. 1, with the off-center intensity of the pulse 5 at the receiving means 9 dropping off rapidly to each side of the axis of the pulse 5, which is intended for the sensors $S_1$ and $S_3$ and which is diagrammatically represented by the pulse components 55 and 59 in FIG. 1.

The receiving means 9 also generally includes noise avoidance means, such as a plurality of electronic filters 61, one for each of the sensors 47, designated "$F_1$", "$F_2$", and "$F_3$" in FIG. 1. Each of the filters 61 is designed to recognize the signature impressed on the pulse 5 by the transmitter 13, such that the emitted pulse 53 can be readily separated electronically from undesired ambient and flange noise interference signals received by the sensors 47.

The system 1 may also include auxiliary filtering means (not shown), which are adapted to filter extraneous corruptions of the pulse train arising from interferences caused by chemical and metallurgical influences arising from material variations and rail length variations of the individual sections used to construct the rail 7. For example, the auxiliary filtering means may include computer software contained by the data processor 11, which is designed by methods commonly known in the art, to remove such influences from data contained in the emitted pulse 53.

Outputs from the filters $F_1$, $F_2$ and $F_3$ are fed into a digitizer 63, which converts the signal amplitude respectively received by the sensors $S_1$, $S_2$ and $S_3$ to digital data which the data processor 11 analyzes. A displacer mechanism 65, such as a servomechanism in combination with a hydraulically activated linear motor or other suitable arrangement commonly known in the art, is adapted to increase or decrease the displacement between the transmitting means 3 and the receiving means 9, as controlled by the processor 11, whereby maximum signal intensity of the pulse 53 is received by the sensor $S_2$ and lesser, approximately equal, signal intensities are received by the sensors $S_1$ and $S_3$.

For those instances where the signal intensity received by the sensor $S_2$ is not greater than the signal intensities received by each of the sensors $S_1$ and $S_3$, or the signal intensity received by one of the sensors $S_1$ and $S_3$ is greater than that received by the other one of the sensors $S_1$ and $S_3$, the data processor 11 will activate the displacer 65 such that the distance between the transmitting means 3 and the receiving means 9 is increased or decreased, as logically appropriate, whereby the signal intensity received by the sensor $S_2$ is greater than the signal intensities received by each of the sensors $S_1$ and $S_3$ and the signal intensities received by each of the sensors $S_1$ and $S_3$ are substantially equal, a configuration sometimes referred to herein as an "equilibrium" configuration.

As the rail 7 of a continuous track is formed, rail sections 67 are aligned in an end-to-end configuration, as schematically shown in FIG. 1. The rail sections 67 are generally fixedly secured together with a pair of splines 69 connected by a plurality of through bolts 70 extending therebetween. Thus, a gap, barrier or boundary 71 is formed between the adjacently spaced rail sections 67. As the vehicle 17 moves along the rail 7, the boundary 71 prevents the refracted pulse 37 from being transmitted along the rail 7. Due to such interference by the boundary 71, the signal intensities received by the sensors $S_1$, $S_2$ and $S_3$ become unstable, unpredictable or non-existent. Such interference can also be caused by mud or other obstruction of the rail 7, such as at a railroad crossing, or the like. Under such conditions, the data processor 11 will cause the displacer 65 to unsuccessfully seek the equilibrium configuration.

As a result, the system 1 includes a rail splice or boundary detector 73 positioned near the front of the vehicle 17, such as an ultrasonic transmitter/receiver 75 (FIG. 7) whereby a series of pulses 77 are transmitted generally vertically. The pulses 77 are directed such that one of the splines 69 passing below the transmitter/receiver 75 will reflect a component 79 of the one or more of the pulses 77 back to the transmitter/receiver 75. The data processor 11 is adapted to compare the combined transit time of the pulses 77 and 79 with the transit time anticipated for reflections from one of the splines 69.

If the observed transit time is greater or less than the anticipated transit time, the reflected pulse 79 will be ignored and the system 1 will attempt to maintain the aforesaid equilibrium configuration. If the observed transit time is approximately equal to the anticipated transit time, the data processor 11 is adapted to place the displacer 65 on standby to thereby avoid seeking for the equilibrium configuration which would be unsuccessful due to the interference caused by the boundary 71.

The data processor 11 is adapted to continue to maintain the displacer 65 in standby until the vehicle 17 has traveled a sufficient distance along the rail 7 whereby the boundary 71 corresponding to the spline 69 detected by the boundary detector 73 no longer interferes with the refracted pulse 37. For example, in one application of the present invention, the data processor 11 automatically placed the displacer on standby for a distance of approximately 39 inches along the track 7 immediately following the detection of one of the splines 69.

A displacement encoder 81 monitors the changes in longitudinal displacement between the transmitting means 3 and the receiving means 9 and communicates such information to the data processor 11 for use in determining the transit time of the refracted pulse 37 through the rail 7, as hereinafter described.

The system 1 includes a rail height detector, such as an ultrasonic transmitter/receiver 83, which transmits a longitudinal ultrasonic pulse 85 at normal incidence or perpendicular to the rail 7. As the pulse 85 encounters the rail 7, a first echo portion 86 of the pulse 85 is reflected from the top of the rail 7 such that a first echo is received by the rail height detector 83. A portion 87 of the pulse 85, which enters the rail 7, traverses the rail web 41 and a second echo portion 88 thereof is internally reflected from a bottom surface 89 of the rail base 43, which causes a second echo to be received by the rail height detector 83.

The data processor 11, in communication with the rail transmitter/receiver 83, is adapted to determine the height of the rail 7 from the time interval between receipt of the first and second echoes from the pulse 85. The rail height detector 83 repeatedly transmits one of the pulses 85, such as every 10 mm. along the rail 7.

In one application of the present invention, the transmitter 13 was spaced near one side of the test wheel 19, and the transmitter of the rail height detector 83 spaced near the opposing side of the test wheel 21, with each operating independently of the other.

The system 1 includes a rail temperature detector 91, such as an infrared temperature detector or other suitable apparatus, which is adapted to remotely measure the temperature of the rail 7. The temperature detector 91 is adapted to dynamically and continuously measure the temperature of the rail 7 as the vehicle 17 travels therealong.

The system 1 includes a site identifier 93, such as a shaft encoder system which locates the position of each of the periodic transmissions of the pulses 5 along the rail 7 relative to a fixed point along the rail 7, or the like. It is foreseen that a GPS (global positioning system) may be included as an integral part of the site identifier 93.

The locations of the pulses 5 are communicated to the data processor 11, which is adapted to make a permanent record of the location and other observed and calculated data as herein described for each of the sites in a rail log 95.

The data processor 11 is adapted to communicate in real-time with the various components or peripheral devices of the system 1, including the transmitting means 3, the receiving means 9, the displacer 65, the rail splice detector 73, the displacement encoder 81, the rail height detector 83, the rail temperature detector 91, the site identifier 93, and the rail log 95. The data processor 11 includes algorithms which are designed to interrelate the inputs from these various peripheral devices to determine the velocity of propagation of the refracted pulse 37 through the rail 7.

The data processor 11 also includes algorithms to determine the longitudinal stress in the rail 7, the corresponding SFT based on the temperature of the rail 7, and the length of rail which needs to be removed or the length of plug (not shown) which needs to be inserted to correct the SFT to the PSFT, for each such site along the rail in order to avoid rail pull-aparts in Winter and rail-buckles in Summer, respectively.

The data processor 11 is adapted to automatically flag the portions of the rail 7 having critical or threshold longitudinal stress levels by conveying such corrective information to a rail marker 97, such as a remotely controlled paint sprayer, which marks the rail 7 with the appropriate corrective information. The marking may be coded to reflect that corrective information, such as pre-selected color coding, dots-and-dashes, or the like.

The system 1 may include a video camera 99 or the like, which is mounted near the front of the vehicle 17 such that the rails 7 of the track can be visually observed. Output from the video camera 99 may be digitized and displayed on a monitor (not shown). If desired, the image from the video camera 99 may be superimposed on an image of a preferred separation of the rails 7 on a monitor (not shown) where variations therebetween can be visually observed by a user of the system 1. In addition, the processor 11 may be adapted to sound an alarm if the variation between the rail separation observed by the video camera 99 and the preferred separation exceeds acceptable limits.

The system 1 includes a track gauge correction mechanism 103 (FIG. 3), such as a pair of opposing, transversely oriented rams 102 and 103, as shown in FIG. 3. The rams 102 and 103 are adapted to urge each of the mated pairs of flanged wheels 18 outwardly, such as by a force of approximately 100 pounds or other suitable magnitude, in order to maintain proper alignment of the test wheels 21 and 23 with the respective rails 7.

It is foreseen that the system 1 could be combined with other types of flaw detection apparatus contained on the vehicle 17 whereby a single pass along a CR track could dynamically detect other types of rail defects simultaneously with the dynamic measurement of longitudinal stress in the rails 7.

2. SID Operation

In an application of the system 1, the system 1 is calibrated by positioning the test wheels 21 and 23 on a stress-free portion of the rail 7. The transmitting means 3 is caused to transmit a pulse 5 which is refracted into and longitudinally along the rail 7 through the rail web 41, such as along a path indicated by the solid line designated by the numeral 109 in FIG. 6.

The distance between the transmitting means 3 and the receiving means 9 is adjusted, and the focusser 51 is focused whereby a maximum signal intensity is received by the sensor $S_2$ and lesser, substantially equal signal intensities are received by the sensors $S_1$ and $S_3$. The temperature of the rail 7 is measured by the rail temperature detector 91 and the height of the rail 7 is measured by the rail height detector 83. The data processor 11 then identifies the displacement between the transmitting means 3 and the receiving means 9 as representing zero-longitudinal stress at the measured height of the rail 7 and the measured rail temperature.

The systems 1 are then driven along the track with one of the systems 1 running along the top of each of the rails 7 of the track. The track gauge correction mechanism 101 maintains the systems 1 in proper alignment with the respective rails 7. Unless the rail 7 being measured by a particular one of the systems 1 is at its SFT, the triangulation of the path of the pulse 5 through the rail 7 varies from that during calibration of the system 1, such as along the dotted line designated by the numeral 111 in FIG. 6.

The change from the path 109 to the path 111 corresponds to the longitudinal stress in the rail 7, which alters the velocity of propagation of the pulse 37 through the rail 7, which alters the angle of refraction 39 of the pulse 37.

Due to the change from the path 109 to the path 111, the relative intensities detected by the sensors $S_1$, $S_2$ and $S_3$ also changes. The digitizer 63 digitizes and communicates the relative intensities detected by the sensors $S_1$, $S_2$ and $S_3$ to the data processor 11. The data processor 11 then drives the displacer 65 such that the equilibrium configuration is reestablished, as indicated by the relative intensities detected by the sensors $S_1$, $S_2$ and $S_3$, as hereinbefore described. The change in displacement required to re-establish the equilibrium configuration is communicated to the data processor 11 by the displacement encoder 81. The magnitude of the displacement required to re-establish the equilibrium configuration is sometimes referred to herein as the stress induced linear displacement ("SILD").

For example, a 136 lb./yd. rail having a rail height of approximately 181 mm wherein the transmitting means 3 are displaced 851.6 mm from the receiving means 9 for a velocity of propagation of 3,200 m/s, a change in shear velocity of 72 m/s to 3,272 m/s, which represents a 2.25% variation, requires a change in displacement of 186.1 mm to 1037.7 mm, which represents a 21.85% variation. In other words, the system 1 greatly amplifies the relative variations of the change in displacement relative to the shear velocity of propagation of the shear pulse 37 through the rail 7.

The rail height detector 83 provides inputs to the data processor 11 for correcting the changes in displacement between the transmitting means 3 and the receiving means 9 for changes in the height of the rail 7. Algorithms, a look-up table with values determined either empirically or theoretically, or other suitable reference, is contained in the data processor 11, which correlates the displacement required to re-establish the equilibrium configuration to the longitudinal stress in the rail 7.

The rail temperature detector 91 provides inputs to the data processor 11 whereby the SFT can be determined and compared with the PSFT for that locality. If the calculated SFT lies beyond acceptable limits from the PSFT, the data processor 11 activates the rail marker 97 which marks the rail 7 as appropriate with prescribed corrective requirements.

As the system 1 continues along the rails 7, such as at a speed of approximately 25 miles/hour, the trigger means 16 causes the transmitting means 3 to repeatedly transmit pulses through the rails 7, such as every 20 mm therealong. The site identifier 93 provides inputs to the data processor 11 whereby the transmission location of each of the pulses 5 is identified relative to a selected reference location, such as mile markers along the rails 7, or the like.

The data processor 11 causes the rail log 95 to produce a permanent, tabulated copy of the measured stress and other data corresponding to selected ones of the emitted pulses 5. The data recorded in the rail log 95 can be compared with previously acquired data in order to determine those locations in the rail 7 where deterioration is occurring, as evidenced by a change in calculated SFT where no repairs have been conducted.

3. Angle of Incidence Method of Longitudinal Stress Measurement

A modified rail stress measuring system in accordance with the present invention is schematically shown in FIG. 8 and is generally designated by the reference numeral 120. Many of the characteristics of the modified rail stress measuring system 120 are substantially similar to those previously described for the rail stress measuring system 1 and will not be reiterated here in detail.

The system 120 includes transmitting means 122 for transmitting a pulse 124 at a angle of incidence 125, through an interface 126 at an entry site 128 between a rail 130 and a test wheel 132 containing the transmitting means 122, and along a path 134 through the rail 130. The transmitting means 122 is slidably mounted on an arcuately shaped bracket 136 such that the transmitting means 122 pivots about the entry site 128 as the transmitting means 122 is displaced along the bracket 136.

As longitudinal stresses with the rail 130 change which tends to cause a change in the path 134 as detected by receiving means (not shown), a data processor 138 causes the transmitting means 122 to be displaced relative to the bracket 136, thereby modifying the angle of incidence 125 whereby the path 134 remains unchanged. The change in the angle of incidence 125, sometimes referred to herein as the stress induced angular displacement ("SIAD"), is used to determine the changes in longitudinal stress of the rail 130, as hereinbefore described.

For example, a 136 lb./yd. rail having a rail height of mm wherein the transmitting means is positioned at an angle of 68.6° relative to the entry site 128 for a velocity of propagation of 3,200 m/s, a change in shear velocity of 72 m/s to 3,272 m/s, which represents a 2.25% variation, requires a change in the angle of incidence 125 of 3.6° to 72.2°, which represents a 5.25% variation 4. Differential Pulse Transit Time Method of Longitudinal Stress Measurement Both the angle of refraction and the angle of incidence measurement methods require relatively complex and extremely fast acting mechanical adjustment mechanisms. This adds to the cost, complexity and maintenance requirements of the systems. Accordingly, alternative methods of using ultrasonic signal behavior to determine longitudinal rail stress have been investigated.

In one such method, it has been determined that, when a pair of signature pulse trains are successively emitted into the rail 7, as from transmitter 13 and focusser 51 in FIG. 1, the time difference between equivalent pulses in the pair of received pulse chains varies as a function of the longitudinal rail stress. This relationship is illustrated in FIGS. 9 and 10. Referring to FIGS. 1 and 9, two chains of square wave signature pulses, illustrated by way of example only as including five pulses each, are transmitted at an angle into the rail 87 via the transmitter 13. The pulses are received at the sensor S2, and a trigger circuit 141 is set to trigger a timer circuit 142 in response to a certain pulse count. For example, at the leading edge of the first pulse in the first pulse train, the trigger circuit 141 sends a start signal to the timer circuit 142. Then, at the leading edge of the third pulse in the second pulse train, the trigger circuit 141 sends a stop pulse to the timer circuit 142. The timed differential $\Delta T2$ between the two equivalent received pulses is then sent to the data processor 11. The data processor compares the $\Delta T2$ value with the known value of $\Delta T1$, and calculates the longitudinal stress from this and the other input variables, as explained below. While they are represented as separate circuits in FIG. 1, the trigger circuit 141 and the timer circuit 142 can be programmed functions of the data processor 11.

Referring to FIG. 10, a representative chart of differential transit time vs. Kips of force is illustrated. The chart in FIG. 10 is based upon a nominal increase in longitudinal stress of 1.8 Kips per degree fahrenheit. This number can vary from approximately 1.8 to 2.6 Kips/degree fahrenheit depending upon the degree of restraint of the rail. An industry standard number for 136-lb./yd. rail which is totally restrained is 2.6 Kips/degree F. An American Association of Railroads estimate for a typical working rail is 2.3 Kips/degree F. This value varies with rail metallurgy, size, etc. In FIG. 10, it should be noted that the desired SFT (95 degrees F.) occurs at about 13.31 ms of differential pulse transit time ($\Delta T2$), which is also equal to $\Delta T1$ or the difference between the first and third pulses in the transmitted pulse chains. As the differential transit time increases above 13.31 ms, the Kips number goes negative, indicating tensile stress in the rail, while differential transit times below 13.31 ms indicate compressive stress. The relationship between differential transit time and rail longitudinal stress is virtually a linear function, and, thus, the data processor 11 need only apply the following formula, for a desired SFT of 95 degrees F., to obtain the current stress free temperature of the rail at the measured point:

New SFT=95−((13.31−ΔT2)/0.027).

This formula is valid at a presumed change of 1.8 Kips/degree F. For presumed stress changes other than 1.8 Kips/degree F, the SFT calculated according to the above formula is multiplied by the new presumed change rate divided by 1.8. For example, at the industry standard of 2.3 Kips/degree F, the formula would be as follows:

New SFT=(95−((13.31−ΔT2)/0.027)*2.3/1.8.

In a recent sampling of differential transit time vs. Longitudinal Stress, the following statistical data were derived:

| Regression output: | |
| --- | --- |
| Constant: | 54.02887559 |
| Standard error of Y Est.: | 0.241962706 |
| R Squared: | 0.893400386 |
| X Coefficient: | −1.79892473 |
| Std Error of Coefficient: | 0.089690639 |
| No. of Observations: | 50 |
| Degrees of Freedom: | 48 |

Thus, differential transit time of a received signature pulse has proven to be a very reliable indicator of rail longitudinal stress. Of course, the magnitude of the received pulses has little relevance as long as they are detectable. Therefore, no dynamic mechanical displacement or angular adjustment between receiver and transmitter is essential. Thus, the system 1 illustrated in FIG. 1 can be used with a differential transit method, but the displacer 65 and displacement encoder 81 are optional. The displacer 65 can be utilized to vary the spacing between the transmitter 13 and the sensors S1-S3 to compensate for rail height. This adjustment can also be made initially by hand at the start of a test run.

5. Pulse Count Method of Longitudinal Stress Measurement

FIGS. 11 and 12 illustrate a second relationship between ultrasonic signature pulse characteristics and rail longitudinal stress which can also be used to detect compressive or tensile stress. In a phenomena related to the differential pulse transit time, FIG. 11 illustrates a similar pair of successive transmitted signature pulse chains, each with five pulses. When the transmitted pulse chains reach the track surface, they undergo an immediate refraction since the speed of sound in steel is over twice that in the fluid 25. This refraction initially causes the pulses to partially overlap, resulting in the "transmitted pulses shown in FIG. 11 where pulses i and 2 of the second pulse chain may overlap with pulses 4 and 5 of the first pulse chain, resulting in a vectorial addition of the unrectified pulse train and yielding a total of 8 distinct transmitted pulses as they enter the rail 7. As the pulse chains transit the rail 7, if the rail 7 is under compressive longitudinal stress, the chains actually move toward one another, increasing their overlap, and decreasing the number of distinct pulse which can be detected at the sensor S3. This effect is illustrated by the "compressive stress" pulse pattern in FIG. 11, shown as constituting six pulses. By contrast, if the rail 7 is under tensile longitudinal stress, the pulse chains will actually diverge, resulting in an increase in the number of perceived pulses at the sensor S3, as shown in the "tensile stress" series of pulses illustrated in FIG. 11, where the original ten pulses are reformed. For simplicity of illustration, the overlapped pulses have been shown as rectified and at the same amplitude, although, of course, the amplitude as well as the width of the overlapped pulses would vary. The amplitude variation is also related to the longitudinal stress in the rail 7.

Referring to FIG. 12, a chart of compressive Kips stress vs. pulse count is illustrated. As shown, the signature pulse chains can be timed such that the number of received pulses at the sensor S1 can be directly correlated to a range of compressive stress. At 0 Kips, the number of received pulses is equal to the number of transmitted pulses or eight in this example, since the two pulse trains were initially partially overlapped when transmitted. As the compressive stress level goes above 0 Kips, for example, the pulses in the first and the second pulse chain overlap further within the chain, thus decreasing the number of received pulses below 8. As the Kips numbers go negative, indicating tensile stress, the pulse chains diverge, yielding a greater number of received pulses than the number transmitted. While this relationship does not yield the accuracy and reliability of the differential transit method, it can be accomplished with a minimal amount of signal processing circuitry and computing capability. Therefore, the method can be easily used with a hand-held unit such as a unit 201, to be described below with respect to FIGS. 14 and 15. With such a hand-held unit, a length of track can be surveyed by manually taking readings at regular intervals or as a follow-up to a more detailed analysis by the vehicle mounted system 1, as explained below.

In a recent sampling of pulse count vs. Applied Compressive Stress, the following statistical data were derived:

| Regression output: | |
| --- | --- |
| Constant: | 11.84056557 |
| Standard error of Y Est.: | 5.289150398 |
| R Squared: | 0.788848195 |
| X Coefficient: | 5.529400292 |
| Std Error of Coefficient: | 0.412912559 |
| No. of Observations: | 50 |
| Degrees of Freedom: | 48 |

While the above discussion of the analysis of the signals received by the receiver in the pulse count method has been limited to an actual gross count of the pulses, the potential of this method is not so limited. For example, the pulse transmission and reception method can be analogized to a magnetic bar code system often used in retail inventory and pricing systems. For example, if a signature pulse series is transmitted repeatedly through the same section of rail 7, at the same ambient temperature and therefore, the same longitudinal stress level, the received pulse patterns will be identically repeated as well. Therefore, a detailed analysis of received pulse patterns at different stress levels will reveal a detectable repetition in the patterns at similar stress levels. Accordingly, the received signature pulse patterns can be digitally analyzed and compared against a previously prepared listing of all such patterns. In this fashion, an extremely accurate reading of longitudinal stress levels can be achieved.

6. Signal Relativity Method of Longitudinal Stress Measurement

FIG. 13 illustrates a third relationship between ultrasonic pulse characteristics and rail longitudinal stress which can be used to detect compressive stress. In yet another phenomena related to the differential pulse transit time, FIG. 13 illustrates a pair of transmitted, variable amplitude signature wave signals. As the signature wave signals transit the rail 7, they actually move toward one another, with the nodes and anti-nodes vectorially adding to one another. An amplitude detection capability, which can be a programmed function of the data processor 11, is needed to detect the amplitudes of, for example, the second and third signature waves in the received wave form. The signature waves are configured such that, when the amplitudes of the second and third waves are equal, the tested rail is in a stress free condition, represented by the "0" line in FIG. 13. Amplitude values of the first wave greater than this value indicates compressive stress, while an amplitude less than the reference amplitude indicates tensile stress. The absolute values of the amplitude differences between the detected waves can also be used to determine the approximate values of the compressive or tensile stress. This measurement method is also well suited for application with the hand-held unit 201, as described below.

7. Hand-Held Longitudinal Stress Measurement Apparatus

FIGS. 14 and 15 illustrate the hand-held stress measurement apparatus 201 which is capable of implementing any of the static ultrasonic tests, i.e. differential transit time, pulse count or signal relativity.

The apparatus 201 comprises an ultrasonic transmitter unit 202, an ultrasonic receiving unit 203, a fluid filled transmitting pad 204 and a fluid filled receiving pad 205. A pair of pneumatic fittings 211 and 212 are provided to connect a fluid source to fill the pads 204 and 205, respectively. The fluid contained in the pads 204 and 205 can be an anti-freeze-type material such as the fluid 25 in FIG. 4, or, alternatively, can be an oil, since the transducer (not shown) in the transmitter 202 is spaced from the rail surface less than one half of the wavelength of the transmitted signal, any variation in the velocity of propagation of the pulse 5 through the fluid is inconsequential. In addition, the pads 204 and 205 are resilient, which resiliency provides a better fluid contact, and thus a more reliable transmission of ultrasonic signals into the rail 7, even with an irregular or worn rail surface.

A pair of electrical connectors 213 and 214 are provided to connect various signal processing circuitry to the transmitter 202 and the receiver 203, respectively. An infrared rail temperature detector 215 senses the rail temperature via a sensor 216 and a pair of adjustable magnets 221 and 222 serve to firmly attach the apparatus 201 to a rail to be tested. Each magnet 221 and 222 has a rotatable tab 223 which is connected to raise and lower an internal permanent magnet (not shown) to magnetize or demagnetize, respectively, a pair of steel plates 224. The plates 224 are thus magnetized to connect the apparatus 201 to the test rail and demagnetized to remove it.

The length of the hand-held apparatus 201 is adjustable via a pair of rails 231 and 232 which telescope within a corresponding pair of internal bores 233 and 234, shown in phantom in FIG. 14. Thus, depending upon the height of the rail being tested, (which can be measured by hand) the length of the apparatus 201 can be adjusted to achieve maximum signal strength at the receiver pad 205. A handle 235 is provided to facilitate carrying of the apparatus 201.

8. Operation of Hand-Held Apparatus

As was stated previously, the hand-held apparatus 201 can be used for performing the differential pulse transit time method of FIGS. 9 and 10, the pulse count method of FIGS. 11 and 12, or the signal relativity method of FIG. 13. In performing any of these stress detection methods, the amount of signal processing is minimal, i.e. a trigger circuit along with either a timer, a counter or a digital voltage meter with a read-out is all that is required. This well known circuitry can be incorporated into the receiver and/or transmitter housings 203 and 202, respectively, or can be attached to the terminals 214 and 213. A power supply, preferably in the form of a battery, can also be incorporated or attached in the same fashion. Further analysis of the sensed values of differential transit time, pulse count or amplitude can be manually performed by comparison with a chart, etc., or by a programmed microprocessor attachable via the terminals 213 and 214. Alternatively, the sensed values, along with track locations and rail temperature, can be stored for later downloading into a computer.

9. Alternative Transport Vehicle Design for Stress Measurement System

Figure 16:
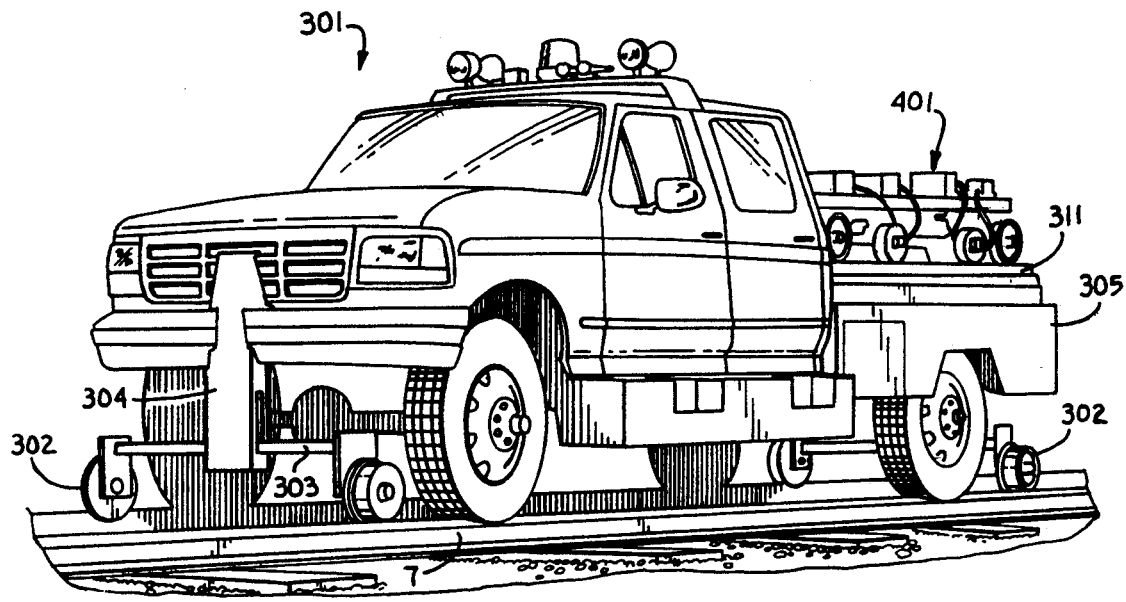
FIG. 16 is a perspective view of an alternative rail vehicle incorporating a longitudinal rail stress measuring system wherein the vehicle incorporates a pair of test rails for initializing the measuring system, with the vehicle illustrated with the stress measuring system placed on the test rails.
Figure 17:
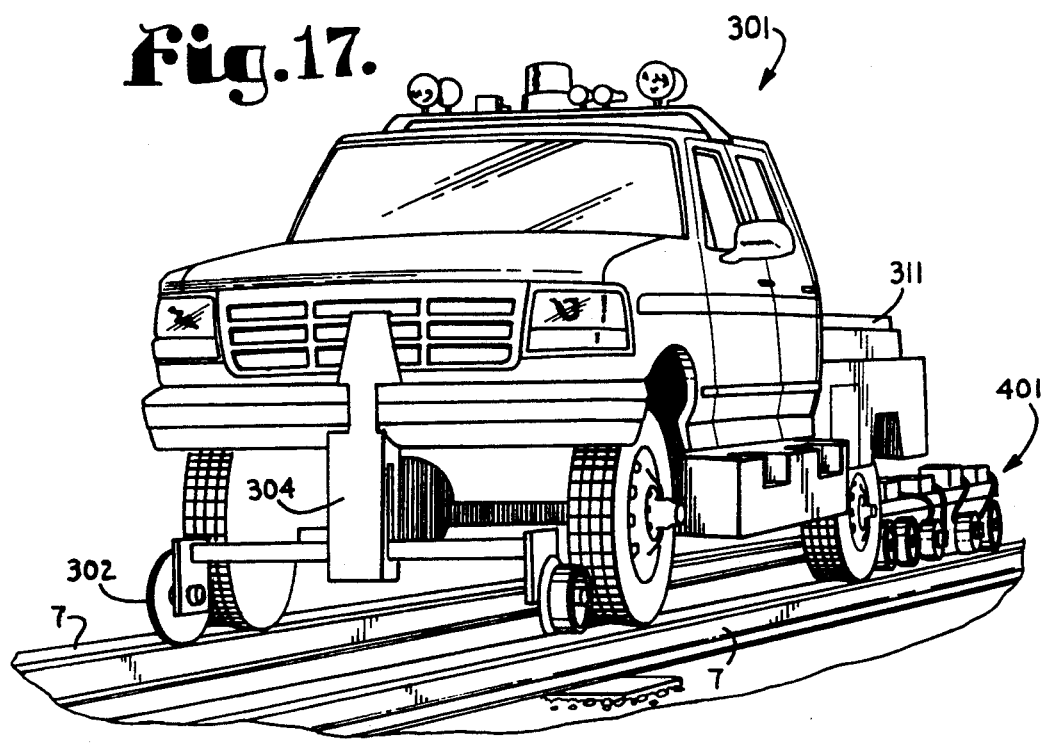
FIG. 17 is another perspective view of the vehicle of FIG. 16, with the stress measuring system removed from the test rails and positioned to be towed behind the vehicle on a length of track to be tested.

FIGS. 16 and 17 illustrate an alternative embodiment of a transport vehicle, designated generally as 301, for transporting a measurement system 401 to a particular track section to be tested. The system 401 is essentially identical to the system 1, except that it is self-contained. Accordingly, the various elements have not been renumbered herein, and reference should be made to FIG. 1 for circuit element representations. Once the desired position is reached, the system 401 is lowered into contact with the track 7 and towed therealong by the vehicle 301.

The vehicle 301, which may comprise a standard truck modified for operation on the railroad track 7, comprises two pair of flanged tracking wheels 302, each attached to a corresponding frame 303. The frames 303 are likewise attached to the vehicle 301 via supports 304. Mounted on a bed 305 of the vehicle 301 are a pair of lengths of standard railroad rails 311. Since it is often difficult or impossible to find a stress free portion of the rail to be tested at the then ambient temperature, the railroad rails 311 are provided as initializing test beds. The rails 311 are not constrained to a particular length and are therefore free to expand and contract with ambient temperature. Thus, the rails 311 are not subject to any longitudinal stress and are thus always in a stress free condition. When the vehicle 301 reaches a desired position for rail testing, a preliminary stress test is made of the stress free rails 311 while the system 401 is still on the vehicle 301. This test, which is preferably performed using the differential pulse transit time method of stress measurement, establishes a baseline pulse differential transit time for a stress free condition at the current ambient temperature. In other words, the base reference numbers for differential transit time, pulse count and/or pulse amplitude are recalculated for zero stress levels as a system check.

Next, the system 401 is lowered onto the rail section 7 to be tested and the vehicle 301 begins towing the system 401 along the rails 7. Periodic pulse transmission and sampling is performed by the system 401, just as described above with respect to the system 1. Thus, every 20 mm, for example, pulse sampling is performed and a cumulative record is kept of rail height, rail temperature and SFT, as calculated by the data processor 11 from the sensed differential pulse transit times. Also, an "event" log is kept which records track separations or other abnormalities. Using the differential pulse transit method of stress detection, the system 1 can be towed at speeds up to thirty miles per hour and still provide reliable information. At these speeds of operation, the received signature pulses will be subject to a Doppler effect, which can easily be accounted for by appropriately programming the data processor 11.

10. Representative Graph of Continuous Test Results

Figure 18:
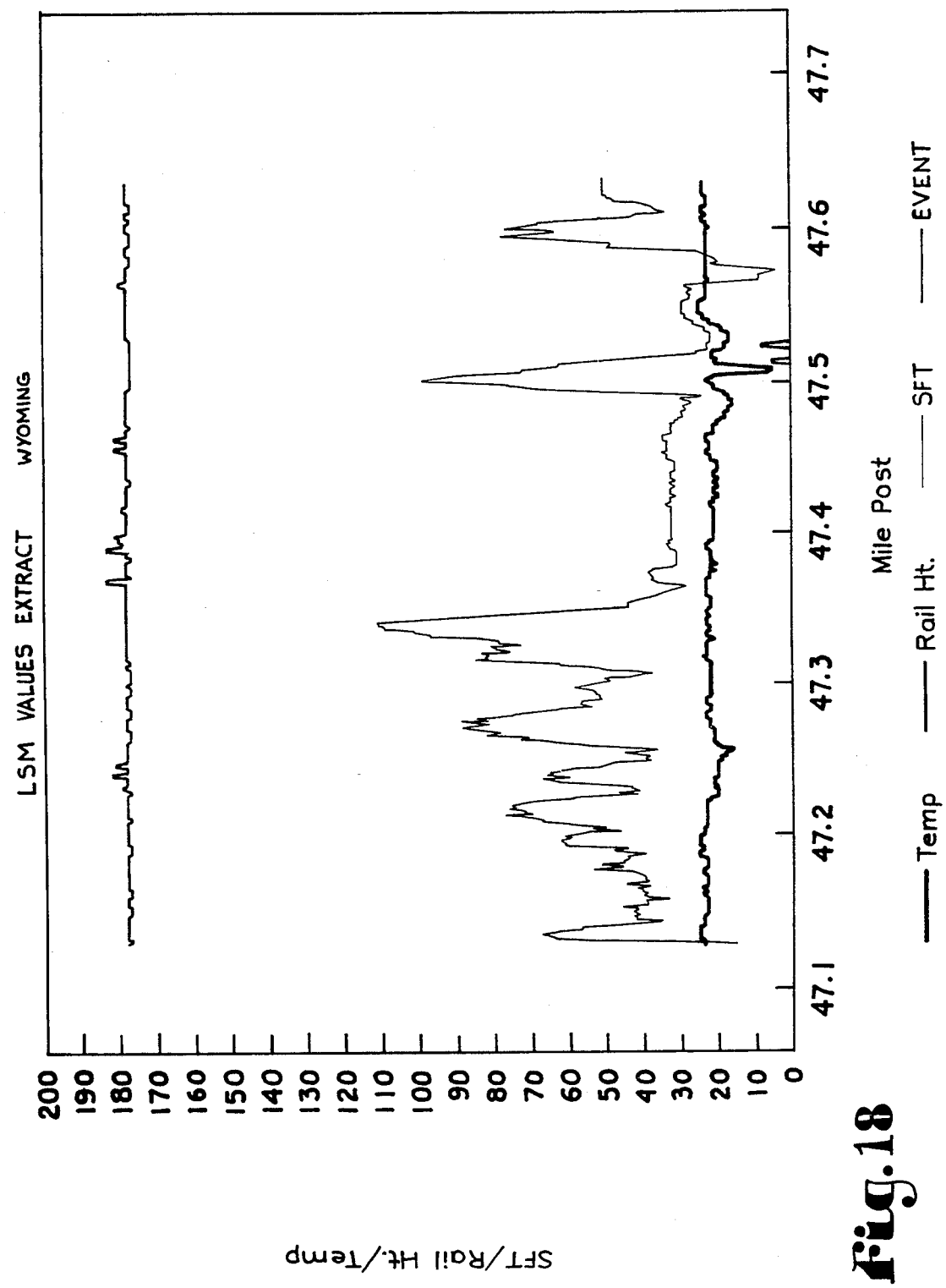
FIG. 18 is a representative read-out from an actual test made along a section of track, illustrating four variables tested and continuously displayed by the stress measuring system.

FIG. 18 is a reproduction of an actual log made by the system 401 as it was towed along a length of track in Wyoming. Keeping in mind the ideal SFT of approximately 95 degrees fahrenheit, it can readily be seen that the actual SFT's along this 0.7 mile section of track vary widely. This can be due to a variety of factors, including the track being initially installed at temperatures other than the ideal SFT, changes in rail conditions subsequent to track installation, changes in track relievability, repairs, etc. At mile post 47.5+, a frozen road crossing was encountered. The low rail temperature and the accompanying high SFT indication at this point is probably due to the relative track condition, i.e. the track base is more firmly anchored and the road bed surface has less resiliency than at other points along the rail.

The system 401 also creates a continuous log as it travels along the rail 7, and the following log was made incorporating a different Wyoming track section than the one in the FIG. 18 graph:

| Milepost | Event | Time |
| --- | --- | --- |
| MP 49.001 | LEFT CURVE | 09:24 |
| MP 49.402 | LR SFT LO | 09:25 |
| MP 49.955 | SIGNAL | 09:25 |
| MP 50.000 | MP RESET | 09:26 |
| MP 50.198 | RIGHT CURVE | 09:26 |
| MP 50.233 | RR LO HT. | 09:27 |
| MP 50.333 | ROAD XSING | 09:27 |
| MP 51.334 | TIE CHANGE | 09:29 |
| MP 51.335 | RR SFT HI | 09:29 |
| MP 51.556 | SWITCH | 09:30 |
| MP 57.987 | LR SFT LO | 09:31 |
| MP 51.999 | LR SFT LO | 09:31 |
| MP 51.000 | MP RESET | 09:31 |
| MP 51.780 | STRUCTURE | 09:32 |

Note that milepost 51.335 is referenced as "RR SFT HI" and a switch at milepost 51.556 is labeled as well. System events, such as curves, road crossings, switches, etc. are detected by the sensor 73 working with the shaft encoder 93, which, as stated previously, can include navigation sensors such as known GPS monitors. The milepost 51.335 will be marked by the rail marker 97 for subsequent testing and/or correction of the rail SFT.

Referring again to FIG. 18, at least two SFT figures are outside of the acceptable ranges for rail SFT, i.e. the high reading at milepost 47.33 and the low reading at milepost 47.57. The question then becomes: Will these SFT levels change back toward the acceptable range with a change in temperature, i.e. will the rail section move with temperature changes sufficiently to prevent the threat of a rail pull-apart or buckling? In order to make this determination, and to provide enhanced accuracy and a redundant check, the system 401 is often pulled over a test section of track twice. If the temperature difference between the morning low and the afternoon high is sufficient, both tests can be made in a single day, i.e. one test early in the morning when the ambient temperatures are lower and then the second test over the same track section during the heat of day. This method thus gives two readouts of SFT for suspect track sections, at two different temperatures, and will indicate whether the rail will correct itself or whether corrective repairs need to be made. In each instance, the system 401 is initialized via the bed mounted stress free rails 311.

Alternatively, if the morning and afternoon temperature extremes are not divergent enough for an accurate assessment of rail flexibility, the tests can be made at different times of the year. With this method, the handheld unit 201 can be ideally used with the vehicle mounted systems 1 or 401. The systems 1 or 401 make a first pass, such as the pass indicated in FIG. 18 when the ambient temperature is approximately 20 degrees. The systems 1 or 401 then marks the suspect rail sections, as explained above. Then, possibly in the summer months with much higher ambient temperatures, a workman makes checks of just those rail sections marked by the earlier test to determine if the rail SFT has shifted toward the safe range. If the SFT is still out of acceptable limits, then corrective action is recommended.

11. Summary

To summarize the Longitudinal Stress Measurement (LSM) system and method, a test system 1, self-contained in a vehicle such as the vehicle 17, or the system 401 towed by a vehicle such as the truck 301, moves along a track section 7 to be tested. The following information is needed, most of which is gathered by the system 1 via the various incorporated sensors:

1. Location of the measurement (Mileposts to 3 decimal places), (provide by the shaft encoder 93);
2. Track Profile (Curve, Tangent, Crossing, etc.) or Event, (provided by the sensor 73 along with the position sensor 93);
3. Individual rail temperature in Degrees Fahrenheit, (provided by the temperature sensor 91);
4. Individual rail height to 2 decimal places, (provided by the detector 83);
5. Individual rail stress value, (as measured by the LSM using any of the ultrasonic testing methods, but preferably by the differential pulse transit time method); and
6. Conversion factor for Kips/Degree Fahrenheit (provided by the railroad being tested).

The calculation of SFT, plotting and log record of the tested tack section 7 is then generated via the following method steps which are processed by the data processor 11:

1. Report the Track Location;
2. Report the rail temperature;
3. Report the rail stress;
4. Report the desired rail SFT;
5. If measured temperature differs from desired SFT, calculate the theoretical rail stress at the measured temperature;

6. Compare the actual measured stress with the theoretical, with the difference being the SFT temperature offset based upon Kips/degree Fahrenheit;
7. Determine the rail size;
8. Compute the actual stress free temperature (SFT);
9. Compare the actual SFT to threshold maximum/minimum values for reporting;
10. Mark the rail with paint at the initial point at which SFT values exceed the thresholds and again when an acceptable range of SFT is reencountered.
11. Report location and value to the printer and/or storage.

In order to make a complete assessment of the rail conditions, a second pass, either by the vehicle mounted systems 1 or 401, or the hand-held unit 201, is made, as detailed above.

In one embodiment of the system 401 and the vehicle 301, the vehicle 301 was a road rail converted Ford F350 with the test carriage 401 winched onto the pair of test rails 311 mounted on the truck bed. The data processing and computation in both the systems 1 and 401 is achieved by an on board Allen Bradley Process Logic Controller (PLC) connected to an IBM compatible computer, which computer is connected to the signal generating and receiving electronics, process control electronics and positioning sensors.

It should be noted that the signature pulse patterns represented in FIGS. 9, 11 and 13 are examples only, and that the differential pulse transit times and pulse count and amplitude charts are achieved with specific signature patterns. The number of acceptable signature patterns is literally infinite, with the only requirement being that the received pulses or waves are recognizable by the data processor 11 as they reach the sensors S1–S3, and that the patterns are exactly repeatable.

It is to be understood that while certain forms of the present invention have been illustrated and described herein, it is not to be limited to the specific forms or arrangement of parts described and shown.

What is claimed and desired to be secured by Letters Patent is as follows:

1. An apparatus for measuring the longitudinal stress in a section of railroad rail, comprising:
   (a) transmitting means for transmitting an ultrasonic signature signal into said section of rail;
   (b) receiving means spaced from said transmitting means for receiving the transmitted ultrasonic signature signal from said section of rail, said received signature signal having been altered by said rail section depending upon the longitudinal stress within said rail section;
   (c) means for processing the altered ultrasonic signature signal to generate a variable dependent upon the longitudinal stress in said rail section; and
   (d) means for calculating the longitudinal stress in the rail section based upon said generated variable.
2. An apparatus as in claim 1, and further including:
   (a) a vehicle for moving said apparatus along said rail, said apparatus making repeated measurements of longitudinal stress at different testing points within each of multiple rail sections of said rail.
3. An apparatus as in claim 2, and further including:
   (a) a rail temperature detector for detecting the temperature of said rail.
4. An apparatus as in claim 3, wherein:
   (a) said rail temperature detector utilizes infrared measuring techniques.
5. An apparatus as in claim 3, and further including:
   (a) a rail height detector for continuously determining the height of said rail.
6. An apparatus as in claim 5, wherein:
   (a) said rail height detector includes an ultrasonic transmitter and detector.
7. An apparatus as in claim 5, and further including:
   (a) a rail position detector for continuously determining the position of said apparatus along said rail.
8. An apparatus as in claim 7, wherein:
   (a) said calculating means further includes means for calculating the stress free temperature of said rail section at each testing point.
9. An apparatus as in claim 8, and further comprising:
   (a) means for maintaining a continuous log of rail conditions as said apparatus is moved along said rail section.
10. An apparatus as in claim 9, wherein:
    (a) said log includes one or more of the following:
        (i) longitudinal rail stress;
        (ii) rail stress free temperature;
        (iii) rail temperature;
        (iv) rail height;
        (v) rail position; and
        (vi) rail events such as crossings, curves, rail boundaries, etc.
11. An apparatus as in claim 2, wherein:
    (a) said transmitting means transmits a series of ultrasonic signature signals, each ultrasonic signature signal being composed of a plurality of ultrasonic pulses; and
    (b) said processing means generates said variable from a measured differential pulse transit time between selected pulses of at least two different signature signals in said series.
12. An apparatus as in claim 11, wherein:
    (a) said receiving means comprises at least one sensor spaced from said transmitting means along said rail.
13. An apparatus as in claim 12, wherein:
    (a) the spacing of said at least one sensor from said transmitting means is variable.
14. An apparatus as in claim 12, wherein:
    (a) said receiving means comprises noise suppression means for suppressing extraneous signals not related to said signature series.
15. An apparatus as in claim 12, wherein said transmitting means comprises:
    (a) an ultrasonic generator means; and
    (b) a wheel containing said generator means, said wheel being in contact with said rail and being filled with a fluid adapted to provide a reliable conduction medium for said ultrasonic signals from said generator means into said rail section.
16. An apparatus as in claim 1, wherein:
    (a) said transmitting means and said receiving means are contained at either end of an elongate portable, hand-held frame; and
    (b) said frame is adjustable lengthwise such that the spacing between said transmitting means and said receiving means can be varied.
17. An apparatus as in claim 16, wherein:
    (a) said hand-held frame comprises means for attaching said apparatus to said rail section.
18. An apparatus as in claim 17, wherein:
    (a) said means for attaching said apparatus to said rail section includes a surface which can be selectively magnetized and demagnetized.
19. An apparatus as in claim 16, wherein:

(a) said apparatus further includes a rail temperature sensor.

20. An apparatus as in claim 16, wherein:
(a) said processing means and said calculating means are removably attachable to said transmitting means and said receiving means.

21. An apparatus as in claim 16, wherein:
(a) said transmitting means transmits a series of ultrasonic signature signals, each signature signal being composed of a plurality of ultrasonic pulses; and
(b) said processing means generates said variable from the differential transit time between selected pulses of at least two different signals of said series which reaches said receiving means.

22. An apparatus as in claim 16, wherein:
(a) said transmitting means transmits a series of signature pulses into said rail section; and
(b) said processing means generates said variable from the number of pulses reaching said receiving means.

23. An apparatus as in claim 16, wherein:
(a) said transmitting means transmits a series of ultrasonic waves into said rail; and
(b) said processing means generates said variable from the amplitude of one or more of the waves reaching said receiving means.

24. An apparatus for dynamically measuring the longitudinal stress in a section of railroad rail, comprising:
(a) transmitting means for transmitting a series of ultrasonic signature signals into said section of rail;
(b) receiving means spaced from said transmitting means for receiving the transmitted ultrasonic signature signals from said section of rail, said received signature signals having been altered by said rail section depending upon the longitudinal stress within said rail section;
(c) means for processing the received, altered ultrasonic signature signals to generate a variable dependent upon the longitudinal stress in said rail section, said variable being determined from said alteration of said signature signals;
(d) means for calculating the longitudinal stress in the tested rail section based upon said generated variable; and
(e) a vehicle for moving said apparatus along said rail, said apparatus making repeated measurements of longitudinal stress within each section of said railroad rail as said vehicle moves along the rail.

25. An apparatus as in claim 24, and further including:
(a) a rail temperature detector for detecting the temperature of said rail.

26. An apparatus as in claim 25, and further including:
(a) a rail height detector for continuously determining the height of said rail.

27. An apparatus as in claim 26, and further including:
(a) a rail position detector for continuously determining the position of said apparatus along said rail.

28. An apparatus as in claim 27, and further including:
(a) means for maintaining a continuous log of rail conditions as said apparatus is moved along said rail.

29. An apparatus as in claim 28, wherein:
(a) said log includes one or more of the following:
(i) longitudinal rail stress;
(ii) rail stress free temperature;
(iii) rail temperature;
(iv) rail height;
(v) rail position; and
(vi) rail events such as crossings, curves, rail boundaries, etc.

30. An apparatus as in claim 24, wherein:
(a) the spacing of said receiving means from said transmitting means is variable.

31. An apparatus as in claim 24, wherein:
(a) said receiving means comprises noise suppression means for suppressing extraneous signals not related to said signature series.

32. An apparatus as in claim 24, wherein:
(a) each of said ultrasonic signature signals is composed of a plurality of ultrasonic pulses; and
(b) said processing means generates said variable from a measured differential pulse transit time between selected pulses of at least two different signature signals in said series.

33. An apparatus as in claim 24, wherein:
(a) each of said ultrasonic signature signals is composed of a plurality of ultrasonic pulses; and
(b) said processing means generates said variable from the number of pulses reaching said receiving means.

34. An apparatus as in claim 24, wherein:
(a) each of said ultrasonic signature signals is composed of at least one ultrasonic wave; and
(b) said processing means generates said variable from the amplitude of one or more of the waves reaching said receiving means.

35. A method of determining the longitudinal stress in a section of railroad rail, comprising the steps of:
(a) transmitting a series of ultrasonic signature signals into said rail at a point in said rail section;
(b) receiving said ultrasonic signature signals from said rail at another point in said rail section, said received signature signals having been altered by said rail section depending upon the longitudinal stress within said rail section;
(c) processing said received altered signals to yield a variable dependent upon the alteration of said signature signals by said longitudinal stress within said rail section; and
(d) calculating said longitudinal stress based upon said variable.

36. A method as in claim 35, and further comprising the steps of:
(a) detecting the temperature within said rail section;
(b) detecting the rail height of said rail section; and
(c) using said rail temperature, said rail height and said calculated stress to calculate the stress free temperature of said rail section.

37. A method as in claim 35, and further comprising the steps of:
(a) repeatedly transmitting and receiving said signals while moving said points at which said signature signal series transmitted and received; whereby
(b) said longitudinal stress and said stressfree temperature are repeatedly calculated for the entire length of said rail section.

38. A method as in claim 37, and further comprising the step of:
(a) maintaining a log of rail conditions as said transmitting and receiving points are moved.

39. A method as in claim 36, and further comprising the steps of:
(a) using said rail height to adjust the distance between the point at which said signature series signal is transmitted and the point at which said series is received.

40. A method as in claim 35, wherein:
(a) each of said ultrasonic signature signals comprises a plurality of ultrasonic pulses: and
(b) said variable is generated from a measured differential pulse transit time between selected pulses of at least two different ultrasonic signature signals in said series.

41. A method as in claim 35, wherein:
(a) each of said ultrasonic signature signals comprises a plurality of ultrasonic pulses; and
(b) said variable is generated from the number of received pulses.

42. A method as in claim 35, wherein:
(a) each of said ultrasonic signature signals comprises a plurality of ultrasonic waves; and
(b) said variable is generated from the amplitude of one or more of the received waves.

43. A method as in claim 35, and further comprising:
(a) initially transmitting and receiving said series along a length of stress free rail to provide a base value for said variable.

* * * * *